(12) United States Patent
Ali et al.

(10) Patent No.: US 8,410,560 B2
(45) Date of Patent: Apr. 2, 2013

(54) ELECTROMIGRATION REDUCTION IN MICRO-HOTPLATES

(75) Inventors: Syed Zeeshan Ali, Cambridge (GB);
Florin Udrea, Cambridge (GB); Julian William Gardner, Warwickshire (GB)

(73) Assignee: Cambridge CMOS Sensors Ltd., Cambridge (GB)

( * ) Notice: Subject to any disclaimer, the term of this patent is extended or adjusted under 35 U.S.C. 154(b) by 451 days.

(21) Appl. No.: 12/691,104

(22) Filed: Jan. 21, 2010

(65) Prior Publication Data
US 2011/0174799 A1    Jul. 21, 2011

(51) Int. Cl.
*H01L 27/14* (2006.01)
*H01L 21/00* (2006.01)

(52) U.S. Cl. ............... 257/414; 438/48; 438/468
(58) Field of Classification Search .............. None
See application file for complete search history.

(56) References Cited

U.S. PATENT DOCUMENTS

| | | | |
|---|---|---|---|
| 5,285,131 A | 2/1994 | Muller et al. | |
| 5,291,142 A * | 3/1994 | Ohmi | 324/719 |
| 5,345,213 A * | 9/1994 | Semancik et al. | 338/34 |
| 5,464,966 A * | 11/1995 | Gaitan et al. | 219/544 |
| 5,500,569 A | 3/1996 | Blomberg et al. | |
| 5,644,676 A | 7/1997 | Blomberg et al. | |
| 5,827,438 A | 10/1998 | Blomberg et al. | |
| 5,831,867 A * | 11/1998 | Aji et al. | 716/112 |
| 5,834,777 A | 11/1998 | Wong | |
| 6,136,619 A * | 10/2000 | Ceuninck et al. | 438/18 |
| 6,297,511 B1 | 10/2001 | Syllaios et al. | |
| 6,597,051 B2 | 7/2003 | Lubomirsky et al. | |
| 7,244,939 B2 | 7/2007 | Stuttard | |
| 7,330,336 B2 | 2/2008 | Luo et al. | |
| 7,495,300 B2 * | 2/2009 | Gardner et al. | 257/414 |
| 7,541,587 B2 | 6/2009 | Cutler et al. | |
| 2002/0142478 A1 * | 10/2002 | Wado et al. | 436/151 |
| 2003/0039586 A1 * | 2/2003 | Toyoda et al. | 422/98 |
| 2004/0074285 A1 * | 4/2004 | Dimeo et al. | 73/31.05 |
| 2004/0075140 A1 * | 4/2004 | Baltes et al. | 257/347 |
| 2005/0199041 A1 * | 9/2005 | Weber et al. | 73/31.06 |
| 2006/0154401 A1 * | 7/2006 | Gardner et al. | 438/53 |
| 2007/0102639 A1 | 5/2007 | Cutler et al. | |

(Continued)

FOREIGN PATENT DOCUMENTS

EP    2 056 337 A2    5/2009
WO    98/32009        7/1998

(Continued)

OTHER PUBLICATIONS

Parameswaran et al., "Micromachined Thermal Radiation Emitter from a Commercial CMOS Process", IEEE Electron Device Letters, vol. 12, No. 2, Feb. 1991.

(Continued)

*Primary Examiner* — Scott B Geyer
(74) *Attorney, Agent, or Firm* — Renner, Otto, Boisselle & Sklar, LLP (57) ABSTRACT

A micro-hotplate is provided in the form of a device comprising a sensor and one or more resistive heaters within the micro-hotplate arranged to heat the sensor. Furthermore a controller is provided for applying a bidirectional drive current to at least one of the heaters to reduce electromigration. The controller also serves to drive the heater at a substantially constant temperature.

26 Claims, 8 Drawing Sheets

U.S. PATENT DOCUMENTS

| | | | |
|---|---|---|---|
| 2007/0168818 A1* | 7/2007 | Kang et al. | 714/745 |
| 2008/0239322 A1 | 10/2008 | Hodgkinson et al. | |
| 2008/0272389 A1 | 11/2008 | Rogne et al. | |
| 2008/0308733 A1 | 12/2008 | Doncaster | |
| 2009/0151429 A1* | 6/2009 | Jun et al. | 73/31.06 |
| 2009/0312954 A1* | 12/2009 | Utriainen | 702/23 |
| 2010/0133528 A1* | 6/2010 | Moon et al. | 257/43 |

FOREIGN PATENT DOCUMENTS

WO      02/080620 A1      10/2002

OTHER PUBLICATIONS

Bauer et al., "Design and fabrication of a thermal infrared emitter", Sensors & Actuators A 55 (1996) 57-63.

Yusasa et al., "Single Crystal Silicon Micromachined Pulsed Infrared Light Source", Transducers 1997, (proceedings of IEEE 1998), 0-7803-3829-4.

Cole et al., "Monolithic Two-Dimensional Arrays of Micromachined Microstructures for Infrared Applications", IEEE Sensors 1998.

Hildenbrand et al., "Micromachined Mid-Infrared Emitter for Fast Transient Temperature Operation for Optical Gas Sensing Systems", IEEE Sensor 2008.

Ji et al., "A MEMS IR Thermal Source for NDIR Gas Sensors", IEEE 2006.

Spannhake et al., "High-termperature MEMS Heater Platforms" Long-term Performance of Metal and Semiconductor Heater Materials, Sensors 2006, ISSN 1424-8220, pp. 405-419.

Tu et al., "Micromachined, silicon filament light source for spectrophotometric Microsystems", Applied Optics 2002, vol. 42, No. 13, May 1, 2003.

Graf et al., "Review of micromachined thermopiles for infrared detection", Measurement Science and Technology, 18 (2007) R59-R75.

Fordl et al., "A High-Precision NDIR CO2 gas sensor for automotive applications", IEEE Sensors Journal, vol. 6, No. 6, 2006.

Kim et al., "A new uncooled thermal infrared detector using silicon diode", Sensors and Actuators A, 89 (2001) pp. 22-27.

Eminoglu et al., "Low-cost uncooled infrared detectors in CMOS process", Sensors and Actuators A 109 (2003) pp. 102-113.

Barritault et al., "Mid-IR source based on a free-standing microhotplate for autonomous $CO_2$ sensing in indoor applications", Sensors and Actuators A 172 (2011) pp. 379-385.

San et al., "A silicon micromachined infrared emitter based on SOI wafer", Proceedings of SPIE 2008, vol. 6836, 68360N-1.

Weber et al., "Improved design for fast modulating IR sources", J. Micromech. Microeng. 7 (1997) pp. 210-213.

* cited by examiner

ELECTROMIGRATION REDUCTION IN MICRO-HOTPLATES

FIELD OF THE INVENTION

This invention relates to a micro-hotplate with reduced electromigration and ion diffusion.

BACKGROUND TO THE INVENTION

It is known to fabricate micro-hotplates on a silicon substrate consisting of a micro-heater formed within a thin membrane layer (made of electrically insulating layers) that is formed by front or back-etching of part of the substrate. Such micro-hotplates can be used to provide a local temperature (from ambient temperature to 700° C.) with low power consumption (typically from a few mW to hundreds of mW) for use as infra-red sources/emitters or flow sensors, or can be coated with a catalyst or sensing material and used as gas sensors. There is a large number of such devices designed and reported using several different materials for the heater or the membrane. The heater itself can be a MOSFET (EP 0 953 152), polysilicon, or metal resistive heater.

A well known reliability issue with metal heaters is caused by electromigration, which at high temperatures results in an increase in resistance over time and can eventually lead to failure of the device. For example, several studies have been shown platinum heaters failing due to electromigration (e.g. Courbat et al. "Reliability improvement of suspended platinum-based micro-heating elements," Sensors and Actuators A 142 (2008) 284-291).

Electromigration occurs due to the momentum transfer between electrons and ions causing the movement of atoms in the presence of high current densities and the mean time to failure (MTTF) is exponentially dependent on temperature according to Black's equation (based on an Arhenius process). This results in an undesirable increase in resistance over time.

For integrated circuits, this reliability issue due to electromigration has been addressed by increasing the width of the metal tracks, which are carefully designed using Black's equation considering the current flow and the operating temperature. As a result, the effective current density through the metal tracks has been reduced. However, heaters in micro-hotplates operate at much higher temperatures and the required width of the metal tracks is often not feasible due to size constraints. In addition, an increase in the width of the metal track can also lead to high power consumption of the micro-hotplate as these tracks have to be connected from a hot spot to a pad outside the membrane. Therefore there will be an increase in thermal conduction losses resulting in an undesirable effect. There is believed to be a need for another method to improve the reliability of such metal heaters.

It has already been demonstrated that bidirectional current causes much less electromigration than a unidirectional current as disclosed in e.g. Liew et al, "Electromigration interconnect lifetime under AC and pulse DC Stress", Proceedings of IEEE Reliability Physics Symposion 1989, pp. 215-219; Maiz, "Characterisation of electromigration under bidirectional and pulsed unidirectional (PDC) currents", Proceedings of IEEE Reliability Physics Symposion 1989, pp. 220-228. Typically, most tracks in a micro-electronic circuit carry a unidirectional current due to constraints of circuit design (for example due to the direction of current flow in transistors or diodes) and so cannot benefit by the use of bidirectional current. The cited studies have been done to improve the design of existing tracks that already use bidirectional, or pulse voltage (such as AC signal lines or clock lines), rather than investigating specifically the effect of bidirectional current in an integrated circuit.

The use of a bidirectional current in micro-gas sensors has been suggested in various studies. For example, there are instances, in the field of gas sensors, where a bidirectional current is applied to the sensing material, but not to the heater itself. The intention in these cases is to avoid polarization effects in the sensing material, and the heater in these cases is driven by a DC signal. For example, Garcia-Guzman, "Design and simulation of a smart rationmetric ASIC chip for VOC monitoring", Sensors and Actuators B November 2003, 232-243, describes a circuit for switching current polarity applied to the sensing material, but the circuit drives the heater by a DC current.

US 2006/0154401 suggests the possibility of having two heaters in a micro-hotplate with one of the heaters driven by a DC voltage while the other is driven by a low frequency AC signal. However, this is specifically done to modulate the temperature of the micro-hotplate. The DC heater in the system described in US 2006/0154401 could still suffer from electromigration.

Bidirectional current has also been suggested for other devices. U.S. Pat. No. 7,330,336 describes the use of bidirectional current to reduce the effect of electromigration in the heating element of disk drives.

However none of these references teaches the use of bidirectional current to drive a heater of the micro-hotplate to reduce the effect of electromigration such that the reliability of the micro-hotplate is improved.

It is an object of the present invention to reduce the effect of electromigration for improving the reliability of the micro-hotplates.

STATEMENT OF THE INVENTION

According to one aspect of the present invention there is provided a micro-hotplate in the form of a device comprising a sensor and one or more resistive heaters arranged to heat the sensor, wherein a controller is provided for applying a bidirectional drive current to at least one of the heaters to reduce electromigration.

The controller may serve to drive said at least one heater at a substantially constant temperature. Furthermore, the controller may serve to apply a pulsed bidirectional current, preferably supplied by a constant voltage, in which the polarity of the voltage changes within each pulse.

Whilst in the prior art (US 2006/0154401) the bidirectional current is specifically used for temperature modulation, the aim of the present invention is to drive the heater at a constant temperature, using bidirectional current to improve reliability. Furthermore, in the same prior art, the temperature has been modulated using a time constant with a rise time and a fall time of the orders of milliseconds or more. In contrast, in the present invention the temperature is kept constant and the bidirectional pulse is applied optionally with a time constant at least two orders of magnitude smaller than that of US 2006/0154401. Any change in temperature of the heater is not achieved by the use of bidirectional current, but by other means, such as changing a current/voltage level, or changing a pulse width in a pulse width modulation (PWM) system, or turning the heater off for some time while operating in a pulsed mode.

If a sinusoidal type signal is used to apply the bidirectional current, then it preferably has a time period much smaller than the thermal transient time of the micro-hotplate (preferably at least two orders of magnitude smaller) to ensure that the temperature is not altered due to the shape of the signal. If a square wave type signal is used to apply the bidirectional current, then the temperature will remain constant regardless of the frequency as long as the current/voltage level is not altered. The temperature can of course be altered according to the application by changing the voltage/current level, or turning off the heater (such as when used in the pulsed mode)

Driving the heater by means of bidirectional or bipolar current, instead of unidirectional current can greatly reduce electromigration and can improve the lifetime of the micro-hotplate. It also allows more flexibility in the design of the heater, allowing the use of thinner heater tracks where required.

The micro-hotplate can be manufactured by a CMOS compatible microelectronics process, e.g. CMOS and/or silicon on insulator (SOI). In most of these processes, aluminium, tungsten or copper is optionally used as metallization. Aluminium is by far the cheapest but it is worst in terms of electromigration. Its maximum temperature is limited to about 175-200° C. with a resistance which changes at a rate over time. By use of bidirectional current, one can extend the maximum temperature of the micro-heater using aluminium to over 250° C. (e.g. 300° C.) with a resistance whose rate of change over time is the same as it is at 175-200° C. Tungsten is a more robust metal and can withstand higher temperatures. It nevertheless still suffers from electromigration (but to a less extent than aluminium). One can extend the maximum operating temperature of a micro-heater using tungsten from 400° C. to 600° C. by using bidirectional current as described.

According to another aspect of the present invention there is provided a micro-hotplate in the form of a device comprising a sensor and one or more resistive heaters arranged to heat the sensor, wherein a controller is provided for applying a bidirectional drive current to at least one of the heaters to reduce ion diffusion.

If the heater is not made of a metal but made of doped or undoped polysilicon or single crystal silicon, it is possible that at high temperatures (e.g. 600° C.) a slow ion diffusion process can take place which could be affected by the flow of current in one direction. The present invention applies, at least to an extent, to these materials as well. In this arrangement, the bidirectional current could help to slow down the diffusion process in one direction, which could indeed help to minimize the rate of change in resistance over time of the micro-heater.

According to another aspect of the present invention there is provided a method of manufacturing a micro-hotplate in the form of a device comprising a sensor and one or more resistive heaters arranged to heat the sensor, the method comprising: applying a bidirectional drive current to at least one of the heaters to reduce electromigration.

BRIEF DESCRIPTION OF THE DRAWINGS

In order that the invention may be more fully understood, a number of embodiments of the invention will now be described, by way of example, with reference to the accompanying drawings, in which.

DETAILED DESCRIPTION OF THE PREFERRED EMBODIMENTS

Figure 1:
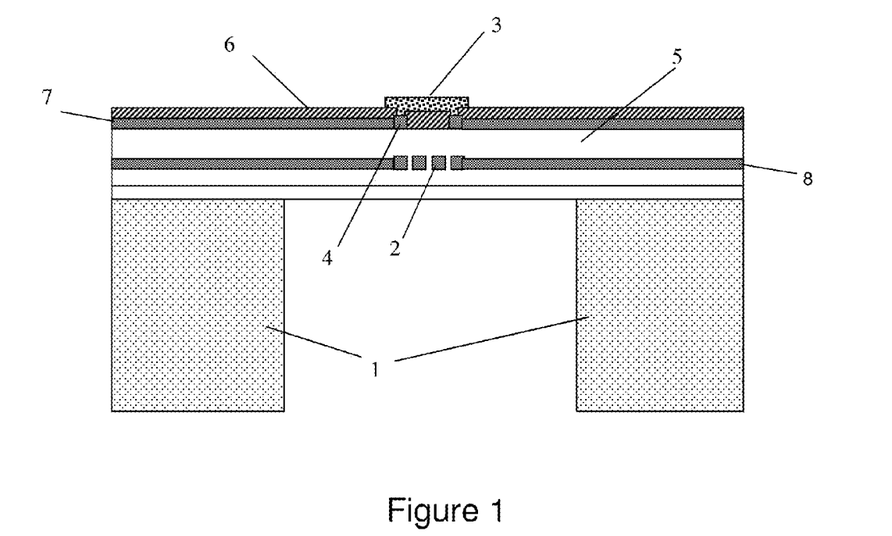
FIGS. 1 to 4 and 7 are schematic cross-sections of a micro-hotplate which can be driven by bidirectional current.

FIG. 1 shows a schematic cross section of a micro-hotplate used for applying a bidirectional current. Optionally, the micro-hotplate of FIG. 1 can be used as a gas sensor. There is provided a membrane layer 5,6 which is supported on a silicon substrate 1, the membrane layer consists of dielectric layers 5 and a passivation layer 6. A resistive heater 2 is formed within the membrane layer and connected to the rest of a chip by tracks 8. It will be appreciated that the resistive heater 2 can also be formed optionally above or below the membrane layer. The gas sensing electrodes 4 are formed from a top metal layer 4. The passivation layer 6 above these electrodes 4 has been removed by etching to allow electrical contact with a gas sensing material 3 deposited on top of the membrane layer. The gas sensing electrodes 4 are also connected by tracks 7 to associated circuitry (see description below with reference to FIG. 9).

The resistive heater 2 may be of any shape, for example, meander, spiral or ring-shaped, or may consist of multiple rings. The gas sensing electrodes 4 can be arranged such that the electrodes are located side by side. Alternatively, the gas sensing electrodes 4 may be interdigitated electrodes, or two concentric electrodes, or may be in any other arrangement that allows a measurement of the material resistance in the presence of a stimulus.

Optionally, the entire micro-hotplate is manufactured by using either a commercial microelectronics process (e.g. CMOS, SOI), or using a customized non standard process process. Optionally, the membrane layer is formed in this case by the use of back etching using deep reactive ion etching (DRIE) technique. The micro-hotplate can be fabricated with or without circuitry on the same chip. There can also be arrays of micro-hotplates on the same chip.

Figure 2:
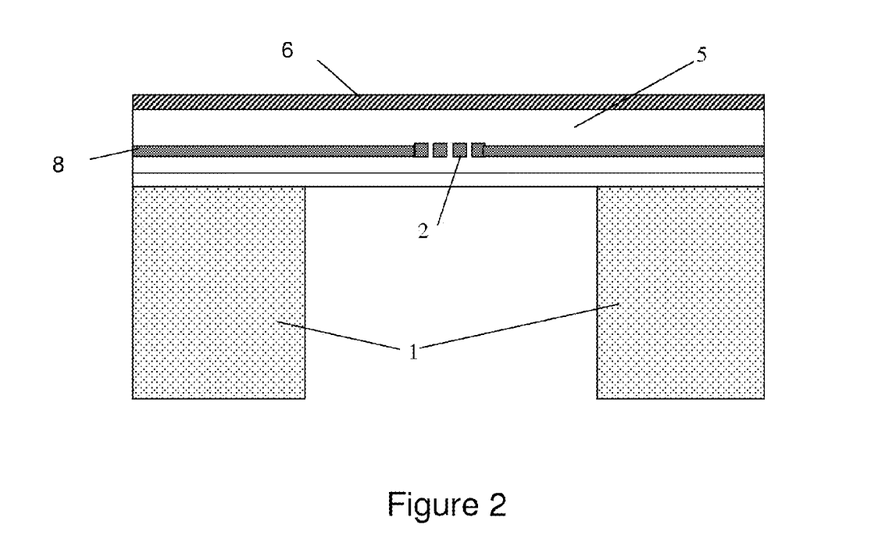

FIG. 2 shows another cross-section of a micro-hotplate used as an IR emitter or a calorimetric gas sensor (by depositing a catalyst on the micro-hotplate). In this type of micro-hotplate, the use of bidirectional current according to the present invention can be useful. Many features in this figure are the same as in FIG. 1, and hence carry the same reference numeral and have the same or a similar function, except that the gas sensing layer 3, the gas sensing electrodes 4 and the tracks 7 (of FIG. 1) are missing. Such a device can also be used as a flow sensor.

Figure 3:
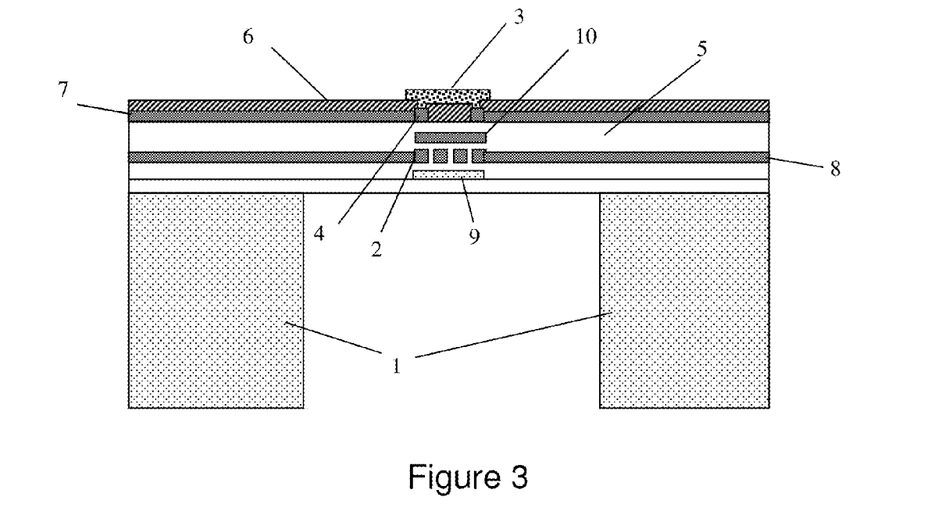

FIG. 3 shows another cross-section of a micro-hotplate in which bidirectional current can be applied in accordance with the present invention. The micro-hotplate of FIG. 3 is similar to that of FIG. 1, but with an additional silicon plate 9 and a metal plate 10 formed within the membrane to improve the temperature uniformity within the heater region. Optionally, the heater 2 as such can be made of a metal layer e.g. aluminium, tungsten, titanium, copper etc.

Figure 4:
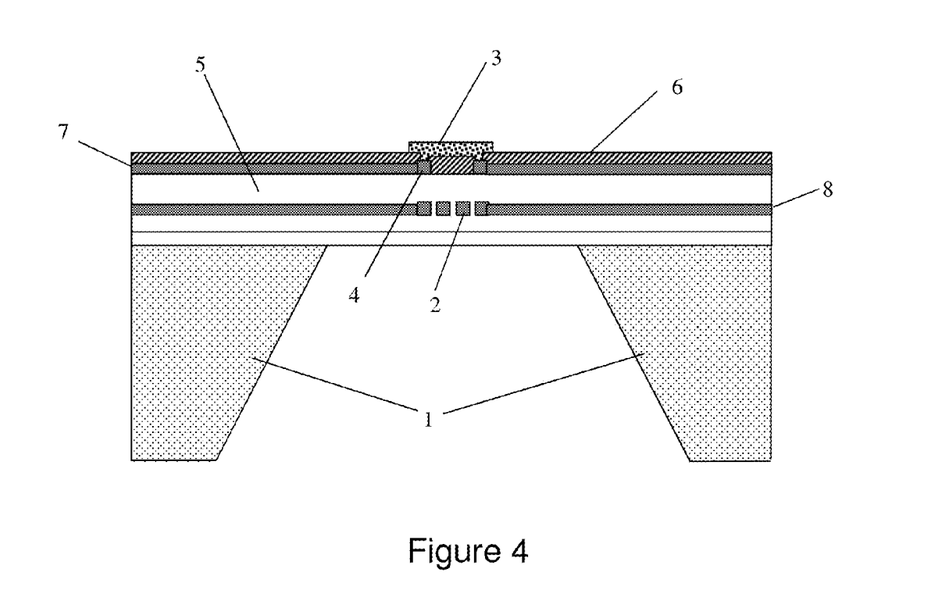

FIG. 4 shows a micro-hotplate where the membrane has been formed by wet etching, optionally by an anisotropic KOH or TMAH back-etch.

Figure 5:
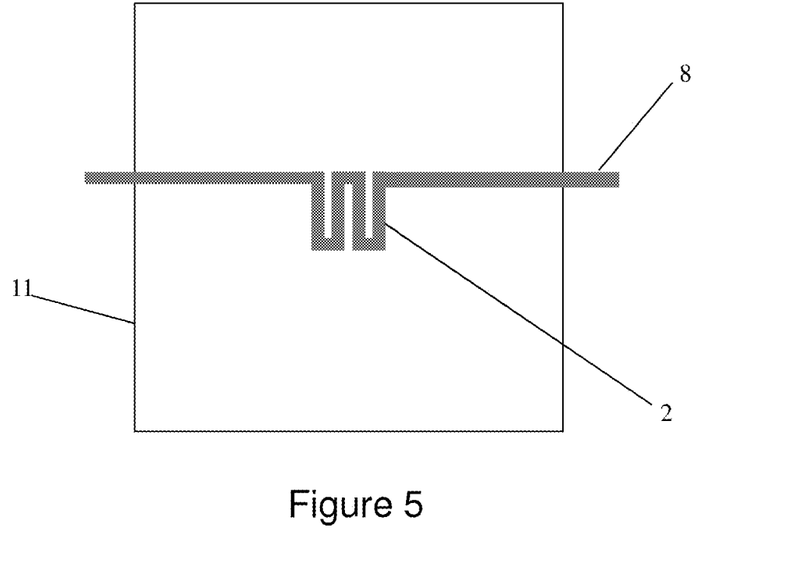
FIGS. 5, 6 and 8 are plan views of a micro-hotplate which can be driven by bidirectional current.
Figure 6:
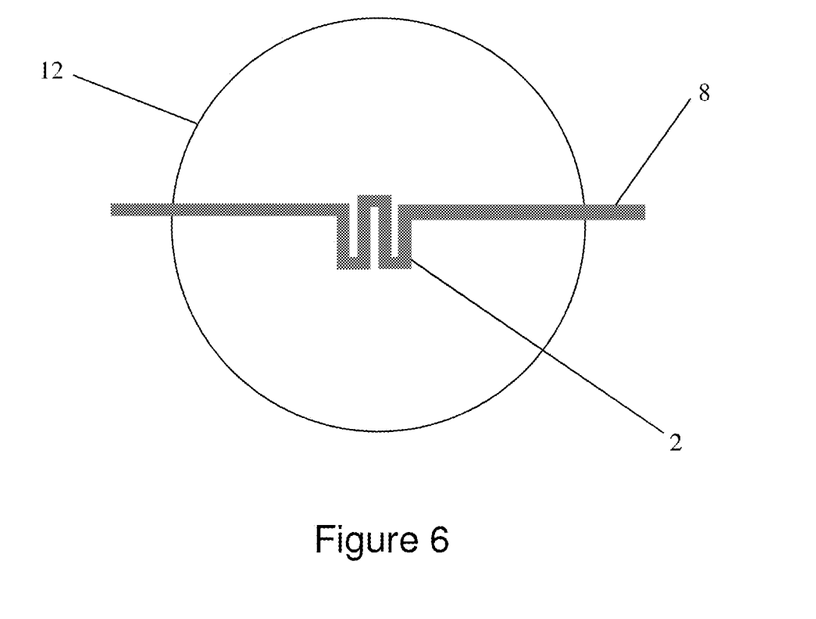

FIG. 5 is a plan view of a micro-hotplate with a meander heater 2 on the square membrane 11. The membrane can alternatively be rectangular. FIG. 6 is a plan view of a micro-hotplate on a circular membrane 12.

Figure 7:
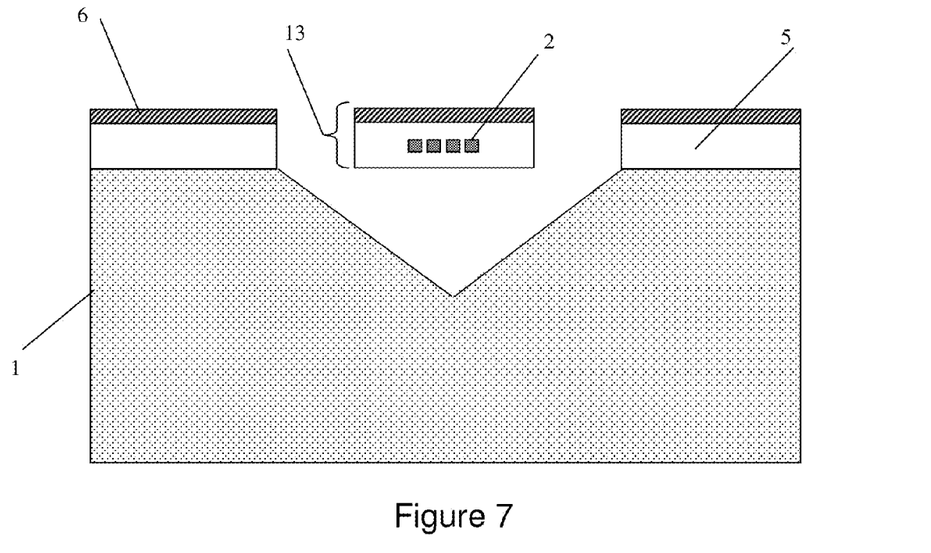
Figure 8:
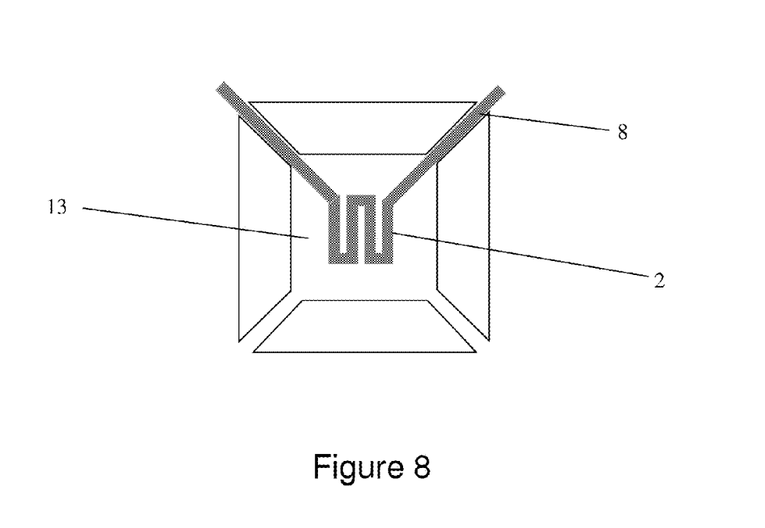

FIGS. 7 and 8 show a micro-hotplate formed on a microbridge using a front side etch. The heater 2 is formed within the micro-bridge 13. It will be appreciated that the heater 2 can also be formed above or below the micro-bridge 13 and gas sensing material or electrodes or heat spreading plate may or may not be provided.

Figure 9:
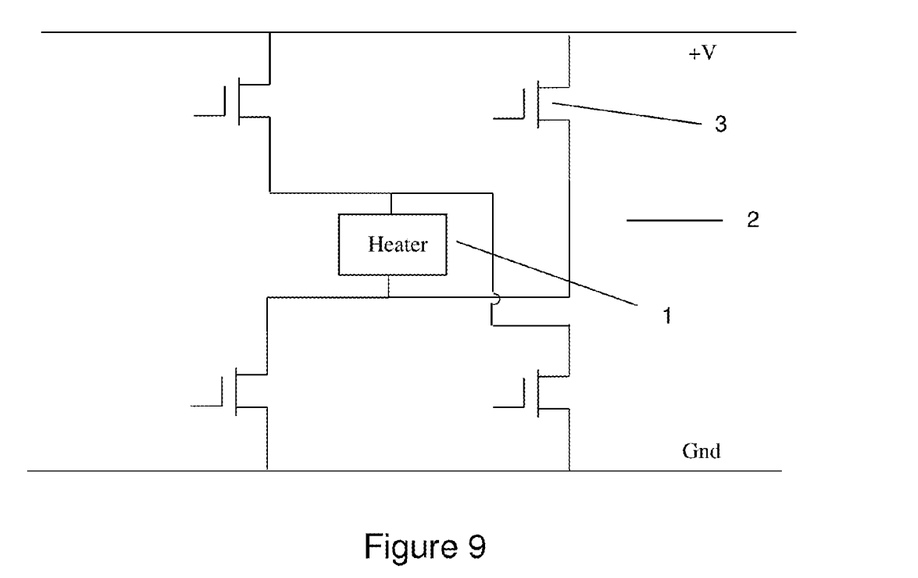
FIG. 9 is a schematic representation of a drive circuit to control the micro-hotplate of FIGS. 1 to 8.

The bidirectional current is applied to the heater of the micro-hotplate by a controller. The controller comprises circuitry to control the bidirectional current. The controller can be integrated within the same chip, or can be connected externally to the chip. FIG. 9 shows a schematic view of a drive circuit having a controller 2 for applying a bidirectional current to a heater 1. In this embodiment, the controller 2 comprises a MOSFET drive circuit. A MOSFET 3 of the drive circuit may be controlled by control electronics from outside the chip. It will be appreciated that the control electronics can be integrated with the heater 1 and controller 2 within the same chip. The control electronics can simply alter the polarity, or can be a complete circuit incorporating a temperature control drive with the PWM system to drive the heater with bidirectional current.

Figure 10:
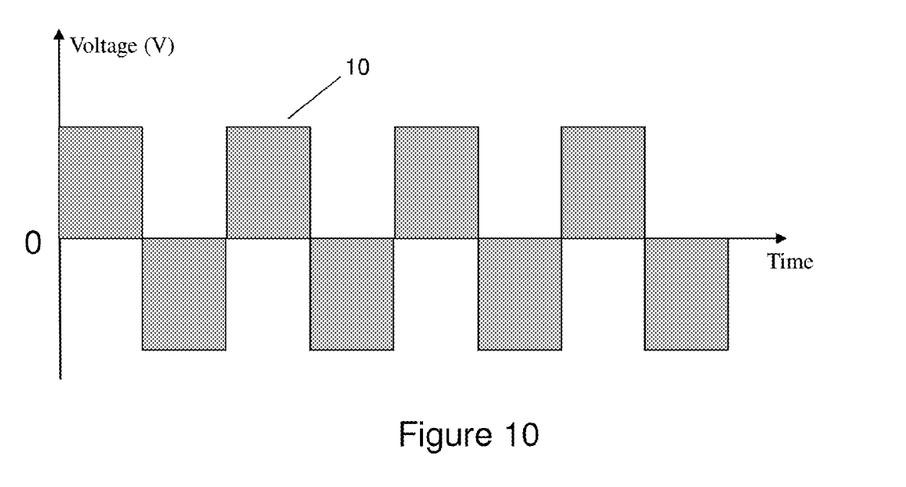
FIG. 10 shows a bidirectional drive current scheme with a square wave signal for the micro-hotplates of FIGS. 1 to 8.
Figure 11:
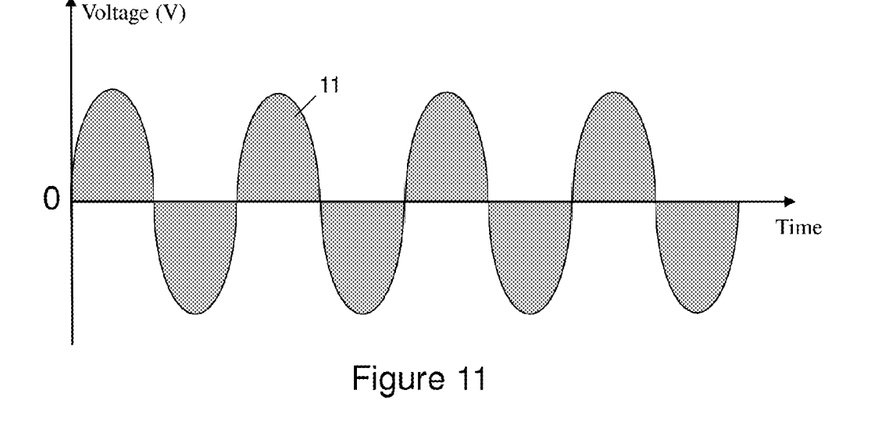
FIG. 11 shows a bidirectional drive current scheme with a sinusoidal wave signal for the micro-hotplates of FIGS. 1 to 8.

The bidirectional current applied to the heater by the controller can be in many forms depending on application. The simplest form is either a sinusoidal or a square wave AC current to the heater as shown in FIGS. 10 and 11. The square wave signal 10 of FIG. 10 can be of any frequency, but the sinusoidal wave signal 11 of FIG. 11 must have a time period much less than the thermal response time of the heater.

Figure 12:
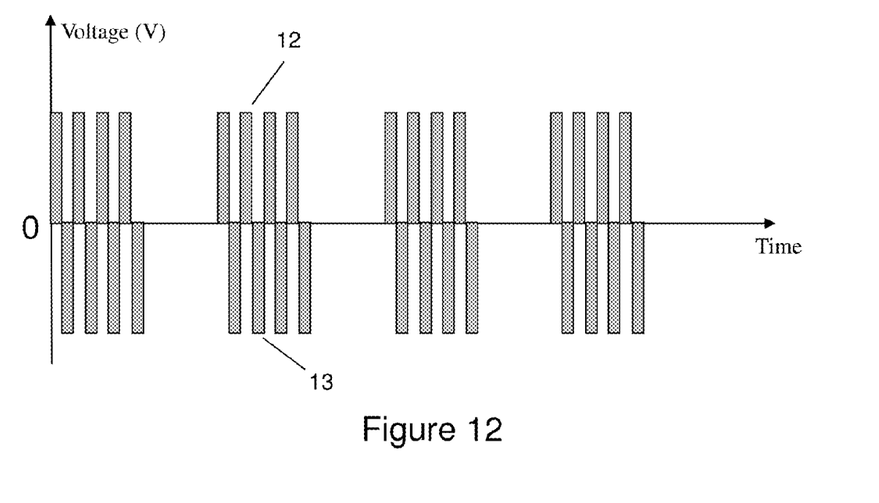
FIGS. 12 to 14 show a bidirectional drive current scheme with a pulse mode signal for the micro-hotplates of FIGS. 1 to 8.
Figure 13:
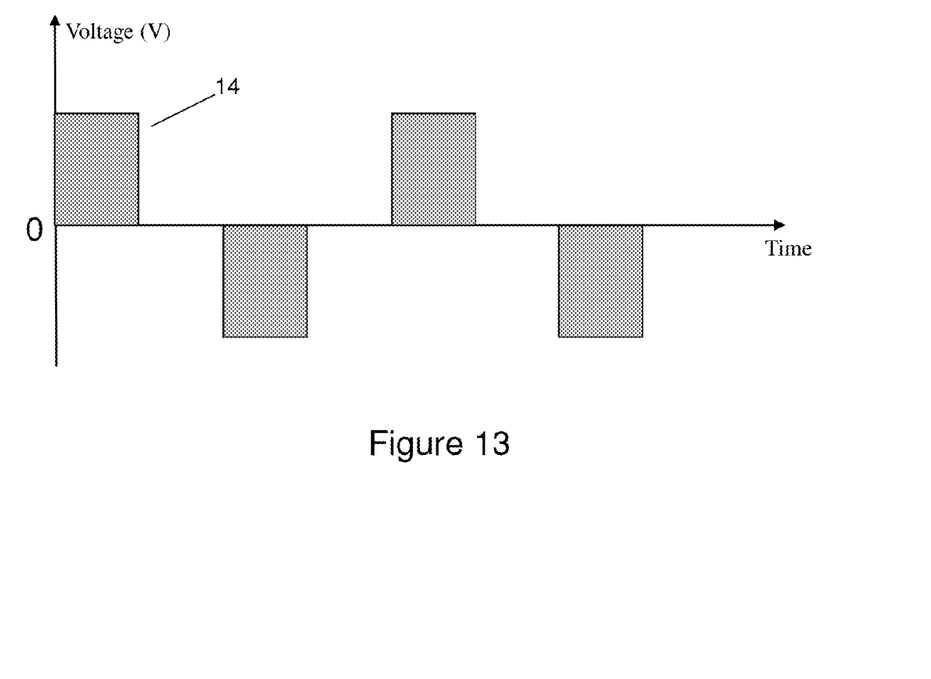
Figure 14:
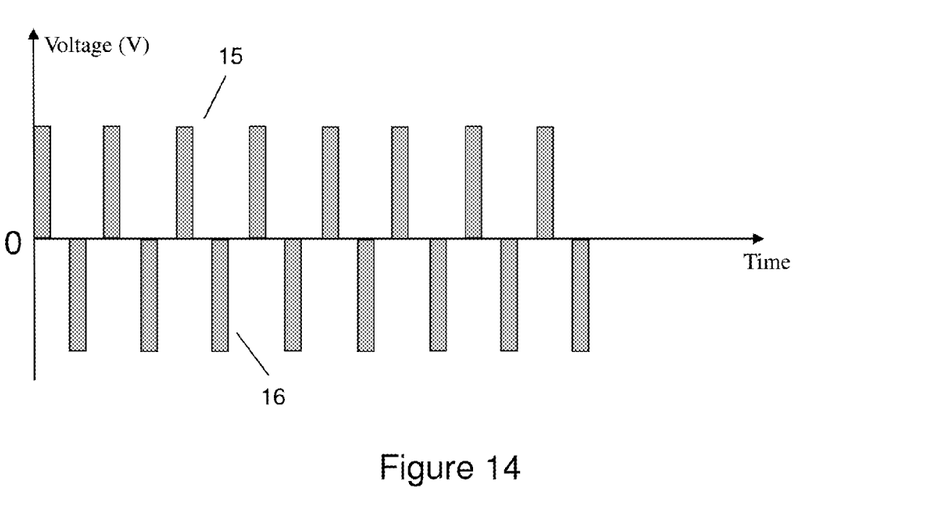

Furthermore, the bidirectional current could consist of pulses as shown in FIGS. 12 to 14. FIG. 12 shows a pulsed bidirectional current in which the polarity of the current changes within a pulse 11, 12.

FIG. 13 is another representation of pulsed bidirectional current in which each pulse has the same polarity within the pulse, but the polarity changes with each pulse 14 or after a certain number of pulses. For example, the pulse may comprise a +5V for 1 s, 0V for 1 s, −5V for 1 s and so on. In both these cases as shown in FIGS. 12 and 13, the width of each pulse, and the spacing between pulses is greater than the thermal transient time of the micro-hotplate.

FIG. 14 is a representation of pulsed bidirectional current, applied by a PWM system, in which each pulse 15, 16 (or a certain number of consecutive pulses) has a different polarity. In this case, the pulse width, and the spacing between each pulse, is less than the thermal transient time, and so the temperature remains constant, and can be controlled by controlling the width of the pulse.

Figure 15:
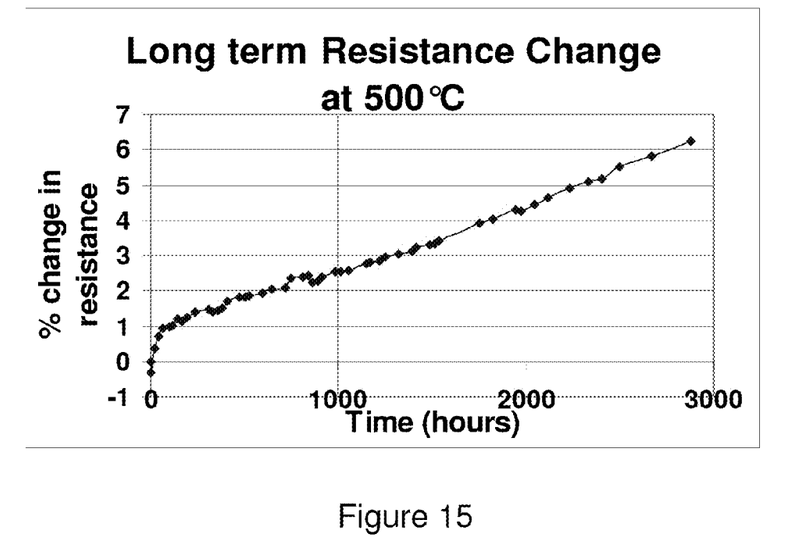
FIG. 15 shows experimental results on the basis of a rate of change in resistance over time for a micro-hotplate driven by unidirectional current.
Figure 16:
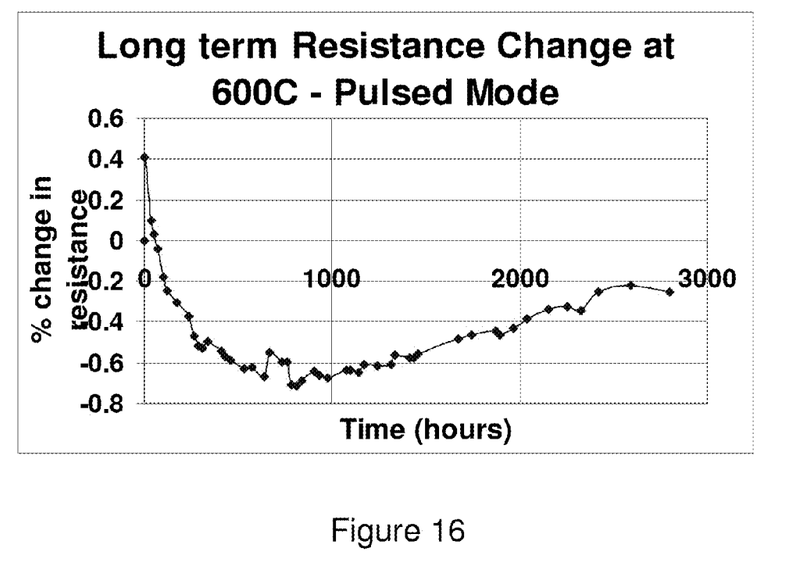
FIG. 16 shows experimental results on the basis of a rate of change in resistance over time for a micro-hotplate driven by bidirectional current.

Bidirectional current can greatly improve the reliability of micro-hotplates, which can be demonstrated from the results of experiments shown in FIGS. 15 and 16. In the experiments, the micro-hotplates have been driven by bidirectional current for a certain number of hours and the reliability of the micro-hotplates is determined by the characteristics of resistance during those hours. FIG. 15 shows a rate of change in resistance over time for a micro-hotplate based on tungsten driven by a simple DC current at 500° C. FIG. 16 shows a rate of change in resistance over time for a micro-hotplate, operated using a bidirectional current with a pulse every 50 ms and an off time of 50 ms. The polarity was changed with every pulse, and the 50 ms time is greater than the transient time of the heater, so the heater was on for 50 ms (at 600° C.), and off for 50 ms. As can be seen, the rate is minimal (and much smaller than that of the micro-hotplate driven by the DC current) when the micro-hotplate is driven by bidirectional current, even at a higher temperature. As a result, the reliability of the micro-hotplates is believed to be significantly improved.

The skilled person will understand that in the preceding description and appended claims, positional terms such as 'in', 'within', 'above', 'below' etc. are made with reference to conceptual illustrations of a micro-hotplate, such as those showing standard cross-sectional perspectives and those shown in the appended drawings. These terms are used for ease of reference but are not intended to be of a limiting nature. These terms are therefore to be understood as referring to a micro-hotplate when in an orientation as shown in the accompanying drawings.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A micro-hotplate comprising a sensor and one or more resistive heaters arranged to heat the sensor, wherein a controller is provided for applying a bidirectional drive current to at least one of the heaters to reduce electromigration.

2. The micro-hotplate according to claim 1, wherein the controller serves to drive said at least one heater at a substantially constant temperature.

3. The micro-hotplate according to claim 1, wherein the controller serves to apply the bidirectional current to said at least one heater but not to at least one other of the heaters.

4. The micro-hotplate according to claim 1 wherein the heater is provided in a dielectric membrane layer supported by a silicon substrate.

5. The micro-hotplate according to claim 1, which has been manufactured by a series of processing steps selected from the group comprising CMOS process and SOI process.

6. The micro-hotplate according to claim 1, wherein the heater comprises a metal selected from the group comprising aluminium, tungsten, copper, titanium and a CMOS metal layer.

7. The micro-hotplate according to claim 1, further comprising at least one heat spreading plate.

8. The micro-hotplate according to claim 1, wherein the controller is a CMOS based electronic circuit, monolithically integrated with the device.

9. The micro-hotplate according to claim 1, wherein the controller is arranged to apply a continuous bidirectional drive current of a form selected from the group comprising a sinusoidal wave and a square wave.

10. The micro-hotplate according to claim 9, wherein the controller serves to control the sinusoidal wave with a time constant substantially less than a thermal transient time constant of the heater.

11. The micro-hotplate according to claim 1, wherein the controller is arranged to apply a pulsed bidirectional drive current in which the direction of the current changes within each pulse.

12. The micro-hotplate according claim 11, wherein the pulsed bidirectional drive current has a pulse period substantially greater than a thermal transient time period of the heater.

13. The micro-hotplate according to claim 1, wherein the controller is arranged to apply a pulsed bidirectional drive current supplied by a constant voltage in which the polarity of the voltage changes within each pulse.

14. The micro-hotplate according to claim 1, wherein the controller includes a pulse width modulation system for driving the heater.

15. The micro-hotplate according to claim 1, wherein the controller includes a MOSFET driver to switch the current polarity of the bidirectional drive current.

16. An array of micro-hotplates located on a chip wherein each micro-hotplate of the array is in accordance with claim 1.

17. A gas sensor, comprising a gas sensing material, and the micro-hotplate according to claim 1.

18. An infra-red emitter incorporating the micro-hotplate according to claim 1.

19. A flow sensor or a sheer stress sensor incorporating the micro-hotplate according to claim 1.

20. A micro-hotplate in the form of a device comprising a sensor and one or more resistive heaters arranged to heat the sensor, wherein a controller is provided for applying a bidirectional drive current to at least one of the heaters to reduce ion diffusion.

21. The micro-hotplate according to claim 20, wherein the heater comprises a semiconductor selected from the group comprising polysilicon and single crystal silicon.

22. The micro-hotplate according to claim 21, wherein the semiconductor is a doped or undoped semiconductor.

23. A method of manufacturing a micro-hotplate comprising a sensor and one or more resistive heaters arranged to heat the sensor, the method comprising: applying a bidirectional drive current to at least one of the heaters to reduce electromigration.

24. The method according to claim 23, wherein said at least one heater is driven at a substantially constant temperature.

25. The method according to claim 23, wherein the heater is formed in a dielectric membrane layer and the membrane layer is formed using a back etching technique.

26. The method according to claim 25, wherein the back etching is carried out by a technique selected from the group comprising deep reactive ion etching and wet etching.

* * * * *